United States Patent [19]

Lundmark

[11] Patent Number: 5,520,908
[45] Date of Patent: May 28, 1996

[54] HAIR, SKIN AND NAIL TREATMENT COMPOSITION AND METHOD

[75] Inventor: Larry D. Lundmark, Prior Lake, Minn.

[73] Assignee: Minnetonka Research Institute, Inc., Minnetonka, Minn.

[21] Appl. No.: 324,517

[22] Filed: Oct. 14, 1994

[51] Int. Cl.$^6$ .............. A61K 7/06; A61K 31/74
[52] U.S. Cl. ............ 424/70.1; 424/78.02; 424/78.03; 424/70.12
[58] Field of Search ............... 424/70, 78.02, 424/78.03

[56] References Cited

U.S. PATENT DOCUMENTS

| | | | |
|---|---|---|---|
| 3,864,288 | 2/1975 | Riew et al. | 260/2 |
| 4,954,532 | 9/1990 | Elliott et al. | 514/846 |
| 5,053,222 | 10/1991 | Taksau et al. | 424/7 |
| 5,059,414 | 10/1991 | Dallal et al. | |
| 5,062,994 | 11/1991 | Imperatori | 252/545 |
| 5,104,646 | 4/1992 | Bolich, Jr. et al. | 424/70 |
| 5,106,609 | 4/1992 | Bolich, Jr. et al. | 424/70 |
| 5,185,155 | 2/1993 | Behan et al. | 424/451 |
| 5,185,325 | 2/1993 | Brawn et al. | 514/23 |
| 5,190,747 | 3/1993 | Sekiguchi et al. | 424/56 |
| 5,194,250 | 3/1993 | Fairhurst et al. | 424/70 |
| 5,230,835 | 7/1993 | DeGuchi et al. | 252/550 |
| 5,242,905 | 9/1993 | Blank | 514/19 |
| 5,269,958 | 12/1993 | De Jager | 252/90 |

OTHER PUBLICATIONS

Sepigel™ 305 publication c/0019/GB/02/May 1993.
CA 121:186779 4 Aug. 1994.
CA 105:11972 1985.
CA 77:46853 1972.

*Primary Examiner*—Paul J. Killos

[57] ABSTRACT

The invention deals with forming stable dispersions or emulsions of hydrated silica which in turn are useful in forming cosmetic compositions such as blends, powders, or sticks useful in treating the hair, skin, or nails.

31 Claims, No Drawings

HAIR, SKIN AND NAIL TREATMENT COMPOSITION AND METHOD

BACKGROUND OF THE INVENTION

1. Description of the Invention

This invention describes compositions containing hydrated silica which may be utilized to treat keratinous substrates such as hair, skin and nails.

2. Description of the Art Practices

U.S. Pat. No. 5,185,155 issued Feb. 9, 1993, to Behan, et al, teaches an encapsulation process employing an aqueous dispersion of silica having a particle size not substantially greater than 100 mm. The compositions of Behan, et al, are disclosed as being useful in flavors, fragrances, and cosmetic ingredients for delayed release.

Elliott, et al, in the U.S. Pat. No. 4,954,532 issued Sep. 4, 1990, teaches the degreasing or moisturizing compositions containing a silanized silica gel, a humectant such as glycerine, and an inert carrier. The composition of Elliott is stated as being useful in treating sebhorreic conditions.

Taksau, et al, in U.S. Pat. No. 5,053,222, issued Oct. 1, 1991, discloses hair cosmetic compositions containing a diester phosphoric acid with ascorbic acid and tocopherol of a particular formula or the salt thereof. The compositions of Taksau may also include some form of silica. Riew, et al, teach in U.S. Pat. No. 3,864,288, issued Feb. 4, 1975, that certain epihalohydrin polymers of high molecular weight may be lightly cross-linked by reaction with a polyamine and quaternized with a tertiary monoamine. The polymers are stated to be excellent thickening agents for water and one of the possible components therein is a form of silica.

de Jager in U.S. Pat. No. 5,269,958, issued Dec. 14, 1993, describes the use of silica and low molecular weight alcohols in dry cleaning formulations. Blank teaches various unsaturated compositions stated to be useful in the treatment of psoriasis in U.S. Pat. No. 5,242,905, issued Sep. 7, 1993. The compositions of Blank may include materials such as silica, ethanol, and propylene glycol.

DeGuchi, et al, in U.S. Pat. No. 5,230,835, issued Jul. 27, 1993, discloses various detergent compositions utilizing an alkyl glycoside, a polyhydric alcohol-polyalkylene oxide adduct and a sulfate ester salt or phosphate ester salt of a polyhydric alcohol-polyalkylene oxide adduct. Quaternary compounds are disclosed for use in the DeGuchi patent. Fairhurst et al, in U.S. Pat. No. 5,194,250, issued Mar. 16, 1993 discloses skin or hair care compositions containing silica with a short chain alkyl ester of a dibasic, tribasic, or tetrabasic carboxylic acid or a hydroxy-carboxylic acid or ester thereof.

Sekiguchi, et al, in U.S. Pat. No. 5,190,747, issued Mar. 2, 1993, discloses oral detergent compositions comprising a nonionic surface active agent which is a fatty acid ester of a hexose sugar or alkyl glycoside thereof. Various quaternary compositions in shampoos are disclosed in the Sekiguchi patent.

Brawn, et al, in U.S. Pat. No. 5,185,325, issued Feb. 9, 1993, discloses hair growth compositions for mammalian skin or hair. Brawn teaches various solvents such as alcohols or powders including fumed silica.

Bolich, Jr., et al, teaches in U.S. Pat. No. 5,106,609 issued Apr. 21, 1992, that a product rheology system was developed containing a nonionic long-chain alkylated water-soluble polymer and a secondary thickening agent which is a water-insoluble surfactant in a compatible solvent. The composition of Bolich is disclosed as being applied to the hair and may include such materials such as silica and quaternary compounds. Similar disclosures are found in Bolich, U.S. Pat. No. 5,104,646 issued Apr. 14, 1992.

U.S. Pat. No. 5,062,994 issued Nov. 5, 1991, to Imperatori teaches skin cleaning compositions in a powder form containing an anionic, amphoteric, nonionic, or cationic cleaning material. U.S. Pat. No. 5,059,414, issued to Dallal, et al, on Oct. 22, 1991, teaches combining two or more separate and distinct cosmetic preparations with independent gelling matrices to obtain a plurality of phases to give a multi-phase, high viscosity, cosmetic product.

Throughout the specification and claims percentages and ratios are by weight and temperatures are in degrees Celsius unless otherwise indicated. Ranges and ratios utilized herein may be combined. To the extent that the cited references herein are applicable to the present invention, they are herein specifically incorporated by reference.

SUMMARY OF THE INVENTION

The present invention contemplates a composition comprising:
 a. a hydrated silica; and,
 b. a quaternary nitrogen compound.

A further aspect of the present invention contemplates a composition comprising:
 a. a hydrated silica; and,
 b. a monohydric alcohol.

A further aspect of the present invention contemplates a composition comprising:
 a. a hydrated silica;
 b. a quaternary nitrogen compound; and,
 c. an alcohol.

Yet another aspect of the invention is a method of emulsifying hydrated silica comprising contacting the hydrated silica with a member selected from the group consisting of water, a quaternary compound and a monohydric alcohol and mixtures thereof for a time and at a temperature sufficient to render the hydrated silica capable of forming an emulsion.

A further aspect of the present invention contemplates a method for treating hair, skin or nails utilizing a composition comprising:
 a. a hydrated silica;
 b. a quaternary nitrogen compound; and,
 c. an alcohol.

DETAILED DESCRIPTION OF THE INVENTION

The various components utilized in the practice of the present invention are as described herein.

THE HYDRATED SILICA COMPONENT

What follows is a description of various forms of silica in order to better define that which is claimed in the compositions of the invention, specifically hydrated silica, as differentiated form other forms of silica.

Fine-particle, synthetic silica are amorphous, submicron size, white powders which have well established utility as abrasive cleaning substances for dentifrice consumer products. In the literature, these products have often been referred to interchangeably as silica, hydrated silica, silicon dioxide, silicic acid, fillers, silica pigments, xerogels, aerogels, amorphous silica, and the like.

Silica can be categorized into two major classes: natural silica and synthetic silica. Natural silica are mined from the ground and are quite different in structure and function than the synthetic silica.

Synthetic silica are of three types: fumed silica, silica gels and precipitated silica and are generally prepared by either a vapor phase process or by a liquid phase process. Fumed silica are products which are synthesized by the vapor process.

Synthetic silica which are derived from a wet process (liquid process) may be categorized as silica gels or precipitated silica. In the Fourth Edition of the CTFA International Cosmetic Ingredient Dictionary the adopted name for the precipitated silica gels is Hydrated Silica. The fumed silica are simply referred to as silica.

Fumed silica are prepared by the hydrolysis of silicon tetrachloride vapor or in a flame of hydrogen and oxygen at an elevated temperature.

Silica gels and precipitated silica are generally prepared by the acidulation of aqueous sodium silicate solution, whereas the precipitated silica are produced under alkaline reaction conditions.

Silica gels are of two types: xerogels and aerogels. During the manufacture of silica gels a hydrosol is first formed followed by the formation of a hydrogel. An aerogel is a hydrogel which is washed and then dried from an organic medium without shrinkage of structure. Xerogels show changes in structure after hydrogel formation.

Three types of particle size structures are known to exist in synthetic silica: primary particles (ultimate particles), secondary particles (aggregates) and tertiary particles (agglomerates). Primary particles are easily seen in fumed silica but are somewhat more difficult to recognize in precipitated silica. It has been claimed that the existence of primary particles in silica gels is purely hypothetical.

Silica gels have internal porosity and a very high BET surface area. Microporosity can be easily created in the precipitated silica during the process of manufacture however they tend to exhibit relatively lower surface areas in comparison to the silica gels.

The surface properties of synthetic silica such as thickening, adsorption and rheological properties are related to the silanol group density of the silica surface and the extent of hydration. There are three types of surface hydroxyl groups present on the surface of synthetic silica: isolated, vicinal (on adjacent silicon atoms) and geminal (two silanols on same silicon atom) silanol groups.

Precipitated silica have very high silanol group densities and fumed silica very low. Silica gels exhibit silanol group density intermediate between the precipitated and fumed silica.

The synthetic silica with which the present invention is primarily concerned are inert, nontoxic, chemically pure, white powders which are acceptable for use under the FDA regulations for use in food and cosmetic formulations.

The description of the individual hydrated silica particles of preference in the present invention are described as having a size in the range of 10 microns to 500 microns, a solubility in water of 50 ppm max at 25° C. and a softening point in the range of 37.7° C. (100° F.) to 93.3° C. (200° F.).

THE QUATERNARY COMPONENT

The quaternary compounds utilized in the present invention may include any of the materials conventionally described as a quaternary compound and in particular the quaternary agents of the formula:

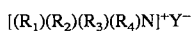

wherein $R_1$ and preferably also $R_2$ represent an organic radical containing a group selected from a $C_{12}$–$C_{24}$ aliphatic radical or an alkyl phenyl or alkyl benzyl radical having 10–16 atoms in the alkyl chain, $R_3$ and $R_4$ represent hydrocarbyl groups containing from about 1 to about 4 carbon atoms and wherein Y is an anion, e.g., fluoride, chloride, bromide, or methylsulfate, and in particular the chlorides.

THE ALCOHOL COMPONENT

The alcohols useful in the present invention are typically those which are non-irritating to the skin. Thus those monohydric alcohols containing from about 12 to about 24 carbon atoms, and especially lauryl, myristyl, cetyl, stearyl, and oleyl and mixtures thereof; dihydric alcohols such as glycols (preferably those having greater 3 carbon and less than 40 carbon atoms); polyhydric alcohols such as glycerine or sugars having polyhydric functionality are included in the scope of the present invention.

AMOUNTS OF THE COMPONENTS

It is suggested in the practice of the present invention that the hydrated silica employed herein be utilized at a weight ratio of about 4:1 to about 1:2 of the quaternary compound. Preferably, the foregoing weight ratio is about 7:2 to about 2:3, and more about preferably 3:1 to 4:5.

The weight ratio of the hydrated silica to the monohydric alcohol are from about 5:1 to about 1:4, preferably about 4:1 to about 1:3, most preferably about 3:1 to about 1:2.

The weight ratio of the water to the hydrated silica in the composition is conveniently about 25:1 to about 1:1, preferably about 15:1 to about 2:1, most preferably about 12:1 to about 3:1.

OPTIONAL INGREDIENTS

Various surfactant ingredients may be employed in the present invention to aid in cleaning the hair, skin or nails. Examples of such materials include the following list of compounds.

Organic, anionic, surface-active, detersive sulfuric acid reaction products to be used in formulating compositions according the present invention are:

Materials such as paraffin sulfonic acid having from about 12 to about 22 carbon atoms, preferably from about 14 to about 18 carbon atoms, and the corresponding sodium-, potassium-, ammonium-, and methyl-, ethyl- or hydroxyethyl- substituted ammonium salts, and mixtures thereof. The paraffin sulfonic acids can be prepared, for example, from n-paraffins derived from straight-run distillates of petroleum or paraffin-base crude oil, reacted with a sulfonating agent, e.g. $SO_3$, $H_2SO_4$, oleum according to known sulfonation processes, as described for example in the British Patent Specification No. 1,111,208, and optionally bleached, hydrated and neutralized. Most preferred are secondary paraffin sulfonates. Specific examples are $C_{14}H_{29}SO_3NA$; $C_{16}H_{33}SO_3NH_4$; $C_{12}H_{29}SO_3Na$; $C_{16}H_{33}SO_3NH_4$; $C_{12}H_{25}SO_3K$; $C_{16}H_{33}SO_3NH(CH_2CH_2OH)_2$; $C_{18}H_{37}SO_3NH_4$; and $C_{22}H_{45}SO_3NH_4$.

Also useful herein are alkylbenzene sulfonic acid, preferably linear alkylbenzene sulfonic acid, having from 8 to 18 carbon atoms in the alkyl radical, and the corresponding sodium-, potassium-, ammonium and substituted ammonium salts, and mixtures thereof. Alkylbenzene sulfonic acids and salts as dodecyl-, tetradecyl- and hexadecylbenzene sulfonic acid can be prepared by reacting the corresponding alkylbenzene compounds with a sulfonating agent as disclosed, for example, in the U.S. Pat. Nos. 2,220,099 and 2,477,383.

Still further useful ingredients include: alkyl sulfuric acid ester, preferably fatty alcohol sulfuric acid ester having from 10 to 22, preferably from 12 to 18 carbon atoms, and the corresponding sodium-, potassium- and ammonium salts, obtained by sulfating hydroxylated hydrocarbons, preferably fatty alcohols having 10 to 22, preferably 12 to 18 carbon atoms, most preferably coconut fatty alcohol having mainly 12 to 14 carbon atoms, with $SO_3$, $H_2SO_4$, etc., according to known processes, followed by hydrolysis and/or bleaching, and neutralized. The alkyl sulfuric acid esters are also known as alkyl sulfates.

Other ingredients include dyes, foam boosters, softening agents, anti-static materials, lotions and cremes.

THEORY OF THE INVENTION

While not wishing to be bound by any particular theory the invention may be better understood by referring to the description given below.

The Liquid Crystalline State of Matter and Mesophases: A mesophase is a state of matter in which there is restricted rotational or translational freedom to molecules under certain special conditions. For example, some materials, when heated, go from the solid state to a mesophase where only partial rotational freedom exists. On the other hand, full or partial translational freedom is present, which results in fluid behavior.

This phenomenon occurs over a defined temperature range before the material melts into an isotropic liquid. Such a mesophase constitutes an ordered fluid phase which has been termed a "liquid crystal". A liquid crystal mesophase has fluidity with a degree of molecular order.

Liquid crystals have the mechanical properties of liquids but retain many of the properties of the solid state (such as optical anisotropy and birefringence). They are easily detected with the aid of a polarizing microscope, under cross-polarizers, where the interference pattern is apparent as a spectacular display.

One classification scheme for liquid crystals has been based on the method by which they are formed or destroyed. Thermotropic liquid crystals are liquid crystalline within a given temperature range. If the existence of the mesophase depends upon the presence of water and the concentration of a material the state of matter is referred to as a lyotropic liquid crystal. Types of molecules which tend to form lyotropic liquid crystals are amphiphilic surfactant molecules where the solvent (water) plays a critical role in the formation of the liquid crystal structure.

Lyotropic liquid crystals are by far the most predominant in cosmetic products. They are known to spontaneously form in many kinds of basic emulsion systems. They are emulsion stabilizers because they impart rigidity and limit compositional fluctuation at the interface when they are present at the oil/water interface.

A variety of chemical substances are presently available to change the condition and properties of hair. Bleaches, permanent waving preparations and dyes can be used to modify the color and style of hair, however some of these preparations can also damage hair.

It is well known that hair has a filamentous structure with an outer shingle-like component called the cuticle and an inner component called the cortex. In virgin, undamaged hair, the cuticle structure is closed and helps to provide natural elasticity. Hair damage, such as that which may be caused by excessive combing, chemical treatments or heat, tends to open or uplift the cuticle, thereby reducing the hair's natural elasticity.

It is common practice to use certain types of hair conditioning treatments to restore elasticity and body to hair which has been subjected to harsh chemical treatment.

Typical hair conditioning treatments utilize a multitude of components to help restore desirable hair properties which may be lost during chemical treatment or to exposure to heat or weathering. One such treatment is a protein pack. Certain botanical extracts, such as chamomile or henna have also been applied to hair to impart shine or luster.

Silicones, volatile silicones and silicone copolymers are often used to facilitate compatibility and to enhance the body of hair. Panthenol is an ingredient which may be utilized to help moisturize and thicken the hair. Synthetic polymers and quaternary ammonium compounds are often used in hair conditioners for their substantivity and film-forming properties.

While it is well known that hair treatment compositions can be formulated which help condition, add shine, moisturize and improve compatibility, these treatments tend to be time consuming and may also over-condition the hair causing it to become limp and loose fullness or body. This is especially the case with fine, thinning hair which tends to be weighed down by excessive deposition of polymeric conditioners.

Accordingly, there exists a need for a hair conditioning composition and method which is easy and quick to use, helps restore natural elasticity and shine, helps smooth the cuticle and improves compatibility and promotes body and fullness without conditioner build up on the hair shaft.

The present invention preferably, but is not required to, provide a hair treatment composition in the form of a liquid-crystalline dispersion which includes a synthetic hydrated silica hair polishing component and a quaternary conditioning agent. It has been found that the composition is useful in a method to condition hair involving applying the preparation to wet hair, massaging to work the composition uniformly over the surface hair cuticles, followed by rinsing and drying.

In a preferred embodiment, the method of use of the hair treatment composition involves shampooing the hair, rinsing, application of the hair treatment composition, gentle rubbing, rinsing and drying.

The hair treatment composition and method of use of the present invention exhibits a number of advantages. First, the present invention helps to smooth uplifted and damaged cuticle by a gentle polishing action attributable to the use of a synthetic silica, which is preferably of the hydrated silica type. The end result is enhanced shine, feel and compatibility which is easily noticed by the user.

Second, a highly effective conditioning action is achieved by utilizing long-chain quaternary ammonium cation micelle deposition on the surface of the synthetic silica (eg. hydrated silica) particle. When rubbed onto the hair cuticle, there is a simultaneous conditioning action which supplements the mild abrasive polishing of the hydrated silica. The end result is polymeric deposition and hair shaft repair without excessive build up on the outer hair surface cuticle. Thirdly, facilitation of the polishing and conditioning action is achieved by suspending the synthetic silica particles in a lyotropic liquid-crystalline dispersion.

The liquid crystalline structure acts as a holding matrix (fixative) for the abrasive synthetic silica particles and helps bring moisture to the hair shaft due to the bound water in the liquid crystal/hydrogel complex. The end result is body and fullness for all hair types, including normal, delicate, coarse, fine and thinning types.

Fourth, the gentle polishing, smoothing action of the liquid crystal/hydrogel complex also benefits the scalp and other skin surfaces by helping to abrade loose skin cells without irritation or harshness to sensitive skin. The end result is soft, smooth skin with less flaking.

The present hair conditioning compositions as preferably formulated include a hydrated silica, one or more quaternary ammonium surfactants and an oil phase and water phase which are in the form of a liquid crystalline dispersion matrix.

The desired liquid crystalline matrix is preferably achieved and maintained by using a mixture of water, Behentrimonium Methosulfate, Cetearyl Alcohol, Cetyl Alcohol and Emulsifying Wax N.F. Typically, the composition will include either the quaternary compound, a primary monohydric alcohol or both.

UTILIZATION OF THE INVENTION

The finished composition of the invention specifically, that containing the hydrated silica, the quaternary component, the alcohol, and/or other cosmetic ingredient components are utilized such that the substrate (hair, skin, or nails) is contacted with an aqueous liquid dispersion or emulsion containing approximately 0.01 to 10.0% hydrated silica, 60 to 90% water with the remainder being the alcohol component and/or other cosmetic ingredients.

The following are Examples of the present invention and comparative examples demonstrating the present invention.

EXAMPLE I

The following is an example of the present invention wherein KERASIL TM 2000 hydrated silica is in the amount of 0.75 parts is combined with 8.75 parts of cetyl alcohol.

The above ingredients may be utilized with other materials to formulate a silica containing emulsion.

EXAMPLE II

A useful product is formulated utilizing 0.75 part of KERASIL TM 2000 hydrated silica and 5.5 parts of a quaternary behenic trimethyl salt.

The foregoing product is useful in preparing a stable emulsion of the hydrated silica in water.

EXAMPLE III

The product of EXAMPLE I is combined with 79.94 parts of water.

EXAMPLE IV

The product of EXAMPLE II is combined with 79.94 parts of water.

EXAMPLE V

Fatty Alcohols and Hydrated Silica

Cetyl alcohol, stearyl alcohol and cetearyl alcohol are each combined with Kerasil brand hydrated silica, cosmetic blends are created with useful properties for hair care and skin care compositions. Such blends are prepared by blending the hydrated silica into a liquid melt of the fatty alcohol at 5° C. above the melting point of the fatty alcohol. After subsequent mixing and cooling, a solid blend composition forms which may be used as an ingredient for cosmetic emulsion products containing hydrated silica.

|  | Premix | | |
|---|---|---|---|
|  | A | B | C |
| Kerasil Hydrated Silica | 1.5 | 1.5 | 1.5 |
| Cetyl alcohol | 8.5 | — | — |
| Stearyl alcohol | — | 8.5 | — |
| Cetearyl alcohol | — | — | 8.5 |

EXAMPLE VI

Quaternary Ammonium Salt/Fatty Alcohol Blends and Hydrated Silica

Incroquat Behenyl TMS is a blend of Behentrimonium Methosulfate and Cetearyl Alcohol manufactured by Croda. When combined with Kerasil hydrated silica, at a temperature 5° C. above the melting point of the Incroquat Behenyl TMS (65° C.), followed by mixing and cooling, a blend is formed with useful properties for hair care and skin care products. Of special interest here, is the use of such blends to form cosmetic emulsions containing lyotropic liquid crystals.

|  | % by weight |
|---|---|
| Kerasil brand hydrated silica | 40 |
| Incroquat Behenyl TMS | 60 |

EXAMPLE VII

| Quaternary Ammonium Salt and Hydrated Silica | |
|---|---|
|  | % by weight |
| Kerasil (Hydrated Silica) | 5.0 |
| Cetrimonium Chloride | 1.0 |
| Water | to 100 |
| Sodium Hydroxide (10%) | (Q.S. to pH 6–7) |

Water is added to a suitable mixing vessel, followed by the addition of the quaternary ammonium salt (Cetrimonium Chloride). The pH is adjusted to a preferred range of 6 to 7. with a suitable base, such as sodium hydroxide. Kerasil hydrated silica is added to the quaternary ammonium salt solution which results in the formation of a Cetrimonium Chloride Hydrated Silica Complex which is isolated by filtration and drying. Said complex has useful properties as a conditioning agent and mild abrasive for keratin substrates such as hair, skin and nails.

EXAMPLE VIII

Use of Hydrated Silica in Cosmetic Creams and Lotions

The products of EXAMPLE V are combined with water, stearic acid, emollients and Triethanolamine (TEA) to make cosmetic emulsions containing hydrated silica:

|  | A | B | C |
|---|---|---|---|
| Premix IA | 2.0 | — | — |
| Premix IB | — | 2.0 | — |
| Premix IC | — | — | 2.0 |
| Stearic Acid | 3.0 | 3.0 | 3.0 |
| Mineral Oil | 4.5 | 4.5 | 4.5 |
| Sesame oil | 3.0 | 3.0 | 3.0 |
| Finsol TN* | 1.5 | 1.5 | 1.5 |
| Germaben II** | 1.0 | 1.0 | 1.0 |
| TEA | 1.0 | 1.0 | 1.0 |
| Water | 84.0 | 84.0 | 84.0 |

*Finsol TN is a C 12–15 alkyl benzoate emollient.
**Germaben II is a preservative from Sutton.

The above compositions have gentle abrasivity due to the inclusion of the hydrated silica which is ideally suited for the treatment of rough nails and nail cuticle.

The formulation examples also serve to illustrate the utilization of hydrated silica in skin care emulsions for the purpose of moisturizing and smoothing dry, rough skin proteins (i.e. keratin).

EXAMPLE IX

Hair Cuticle Polishing and Conditioning Compositions Containing Liquid Crystals and Hydrated Silica The following formulations illustrate the use of Kerasil (Hydrated Silica) in hair conditioning and cuticle polishing compositions; (liquid crystals are observed to be present in the dispersion when viewed with a polarizing microscope at a magnification of 400X):

|  | A | B |
|---|---|---|
| Water | to 100 | to 100 |
| Emulsifying Wax N.F. | 3.00 | — |
| Cetyl Alcohol | 0.75 | 3.00 |
| Kerasil (Hydrated Silica) | 8.75 | 0.25 |
| Stearalkonium Chloride | 0.50 | 1.25 |
| Cetrimonium Chloride | — | 0.35 |
| Crodasone W | 0.25 | 0.10 |
| Incroquat Behenyl TMS | 5.50 | — |
| Mineral Oil | 0.50 | 5.50 |
| Cationic Emulsion 929 | — | 0.50 |
| Glyceryl Stearate | — | 1.50 |
| Panthenol | 0.15 | 0.10 |
| Preservatives | Q.S. | Q.S. |
| Color(s), Fragrance | Q.S. | Q.S. |

EXAMPLE X

Use of Hydrated Silica in Nail Polishing Stick Compositions

A nail polish stick is prepared for followed to be used for buffing to bring the nails to a high transparent gloss. The addition of hydrated silica to such a polishing stick composition enhances polishing efficacy of fats and waxes via the known gentle abrasivity of hydrated silica particles. The following is an example of such a composition:

| NAIL POLISH STICK WITH HYDRATED SILICA | |
|---|---|
|  | % by weight |
| Stearic acid | 10 |
| Carnauba Wax | 10 |
| Beeswax | 10 |
| Isopropyl palmitate | 10 |
| Zinc Stearate | 10 |
| Kerasil hydrated silica | 10 |
| Titanium Dioxide | 40 |
| Fragrance | Q.S. |
| Color | Q.S. |

Procedure: Melt the fats and waxes. Add the pigments and hydrated silica and stir in. Pass through a roller mill for uniformity. Remelt, keep hot for 6–8 hours to allow air to come to top. Scoop off foam, stir slowly and pour the molten liquid into molds. Alternatively, the product may be formed into screw-up stick containers.

What is claimed is:

1. A composition comprising:

a. a hydrated silica; and, b. a quaternary nitrogen compound, wherein the weight ratio of (a) to (b) is about 4:1 to about 1:2.

2. The composition of claim 1 additionally containing water.

3. The composition of claim 1 additionally an alcohol.

4. The composition of claim 1 wherein the quaternary is of the formula:

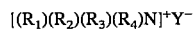

wherein $R_1$ and $R_2$ represent an organic radical containing a group selected from a $C_{12}$–$C_{24}$ aliphatic radical or an alkyl phenyl or alkyl benzyl radical having 10–16 atoms in the alkyl chain, $R_3$ and $R_4$ represent hydrocarbyl groups containing from about 1 to about 4 carbon atoms and wherein Y is an anion.

5. The composition of claim 4 wherein the anion is chloride.

6. The composition of claim 2 containing a weight ratio of the water to the hydrated silica in the composition about 25:1 to about 1:1.

7. A composition comprising:

a. a hydrated silica; and, b. a monohydric alcohol.

8. The composition of claim 7 additionally containing water.

9. The composition of claim 8 containing a weight ratio of the water to the hydrated silica in the composition about 25:1 to about 1:1.

10. The composition of claim 7 wherein the monohydric alcohol contains from about 12 to about 24 carbon atoms.

11. The composition of claim 10 additionally containing a quaternary of the formula:

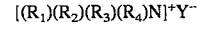

wherein $R_1$ and $R_2$ represent an organic radical containing a group selected from a $C_{12}$–$C_{24}$ aliphatic radical or an alkyl phenyl or alkyl benzyl radical having 10–16 atoms in the alkyl chain, $R_3$ and $R_4$ represent hydrocarbyl groups containing from about 1 to about 4 carbon atoms and wherein Y is an anion.

12. The composition of claim 11 wherein the anion is chloride.

13. The composition of claim 7 wherein the weight ratio of the hydrated silica to the monohydric alcohol is from about 5:1 to about 1:4.

14. The composition of claim 7 wherein the monohydric alcohol is selected from the group consisting of lauryl, cetyl, myristyl, oleyl and stearyl and mixtures thereof.

15. The composition of claim 7 wherein the weight ratio of the hydrated silica to the monohydric alcohol is from about 4:1 to about 1:3.

16. A composition comprising:
   a. a hydrated silica;
   b. a quaternary nitrogen compound; and,
   c. an alcohol.

17. A method of emulsifying hydrated silica comprising contacting the hydrated silica with a member selected from the group consisting of water, a quaternary compound and a monohydric alcohol and mixtures thereof for a time and at a temperature sufficient to render the hydrated silica capable of forming an emulsion.

18. The method of claim 17 wherein the member is at least two members of the group of water, a quaternary compound and a monohydric alcohol.

19. The method of claim 17 wherein the member is all three members of the group of water, a quaternary compound and a monohydric alcohol.

20. The method of claim 17 wherein the quaternary is of the formula:

$$[(R_1)(R_2)(R_3)(R_4)N]^+Y^-$$

wherein $R_1$ and $R_2$ represent an organic radical containing a group selected from a $C_{12}$–$C_{24}$ aliphatic radical or an alkyl phenyl or alkyl benzyl radical having 10–16 atoms in the alkyl chain, $R_3$ and $R_4$ represent hydrocarbyl groups containing from about 1 to about 4 carbon atoms and wherein Y is an anion.

21. The method of claim 20 wherein the anion is chloride.

22. The method of claim 18 wherein the weight ratio of the hydrated silica to the monohydric alcohol is from about 5:1 to about 1:4.

23. The method of claim 22 wherein the monohydric alcohol is selected from the group consisting of lauryl, cetyl, myristyl, oleyl and stearyl and mixtures thereof.

24. The method of claim 18 containing a weight ratio of the hydrated silica of about 4:1 to about 1:2 to the quaternary compound.

25. A method of treating a member selected from the group consisting of hair, skin and nails comprising contacting the member with a composition comprising:
   a. a hydrated silica;
   b. a quaternary nitrogen compound; and,
   c. an alcohol.

26. The method of claim 25 additionally utilizing water.

27. The method of claim 26 containing a weight ratio of the hydrated silica of about 4:1 to about 1:2 to the quaternary compound.

28. The method of claim 25 wherein the monohydric alcohol contains from about 12 to about 24 carbon atoms.

29. The method of claim 25 wherein the quaternary is of the formula:

$$[(R_1)(R_2)(R_3)(R_4)N]^+Y^-$$

wherein $R_1$ and $R_2$ represent an organic radical containing a group selected from a $C_{12}$–$C_{24}$ aliphatic radical or an alkyl phenyl or alkyl benzyl radical having 10–16 atoms in the alkyl chain, $R_3$ and $R_4$ represent hydrocarbyl groups containing from about 1 to about 4 carbon atoms and wherein Y is an anion.

30. The method of claim 28 wherein the anion is chloride.

31. The method of claim 25 wherein the monohydric alcohol is selected from the group consisting of lauryl, cetyl, myristyl, oleyl and stearyl and mixtures thereof.

\* \* \* \* \*